United States Patent
Kinoshita et al.

(10) Patent No.: US 8,952,204 B2
(45) Date of Patent: Feb. 10, 2015

(54) SULFONIUM SALT, METHOD FOR PRODUCING THE SAME, AND PHOTOACID GENERATOR

(71) Applicants: DSP Gokyo Food & Chemical Co., Ltd., Osaka-shi (JP) Tokyo Ohka Kogyo Co., Ltd., Kawasaki-shi (JP)

(72) Inventors: Hironori Kinoshita, Suita (JP); Sumitsugu Kisanuki, Suita (JP); Masaaki Sugi, Suita (JP); Takayoshi Mori, Kawasaki (JP)

(73) Assignees: DSP Gokyo Food & Chemical Co., Ltd. (JP); Tokyo Ohka Kogyo Co., Ltd. (JP)

( * ) Notice: Subject to any disclaimer, the term of this patent is extended or adjusted under 35 U.S.C. 154(b) by 0 days.

(21) Appl. No.: 14/095,870

(22) Filed: Dec. 3, 2013

(65) Prior Publication Data

US 2014/0163254 A1    Jun. 12, 2014

(30) Foreign Application Priority Data

Dec. 7, 2012   (JP) ................................. 2012-268079

(51) Int. Cl.
    *C07C 41/00*         (2006.01)
    *C07C 315/00*      (2006.01)
    *G03F 7/004*        (2006.01)

(52) U.S. Cl.
    CPC .................................... *G03F 7/0041* (2013.01)
    USPC ........................................... 568/633; 568/18

(58) Field of Classification Search
    None
    See application file for complete search history.

(56) References Cited

FOREIGN PATENT DOCUMENTS

| | | | |
|---|---|---|---|
| JP | H08-165290 A | | 6/1996 |
| JP | 2004-334060 A | | 11/2004 |
| JP | 2004334060 | * | 11/2004 |
| JP | 2006-276755 A | | 10/2006 |
| JP | 2008-7410 A | | 1/2009 |
| JP | 2010-215608 A | | 9/2010 |
| JP | 2010-256168 A | | 11/2010 |

OTHER PUBLICATIONS

Derwent World Patents Index Abstract of WO 2003010603, abstract No. 2003:97616 (WO 603).*
Machine Translation of JP 2004-334060.*

* cited by examiner

*Primary Examiner* — Karl J Puttlitz
(74) *Attorney, Agent, or Firm* — Knobbe, Martens, Olson & Bear, LLP

(57) ABSTRACT

A sulfonium salt compound represented by the following general formula (I):

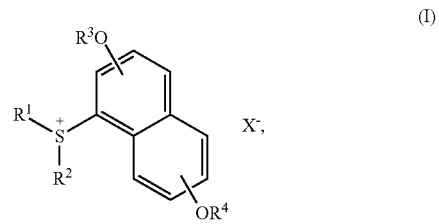

(I)

where $R^1$ and $R^2$ each denote the same or a different alkyl group having 1 to 18 carbon atoms, $R^3$ and $R^4$ each denote the same or a different alkyl group having 1 to 10 carbon atoms, $X^-$ denotes a sulfonate anion or a carboxylate anion, and the substituents denoted by $R^3O$ and $R^4O$ are each located at an arbitrary position selected from the 2-position to the 8-position of the naphthyl group.

4 Claims, No Drawings

SULFONIUM SALT, METHOD FOR PRODUCING THE SAME, AND PHOTOACID GENERATOR

CROSS-REFERENCE TO RELATED APPLICATION

This application claims priority to Japanese Patent Application No. 2012-268079, the disclosure of which is incorporated herein by reference in its entirety.

BACKGROUND OF THE INVENTION

1. Field of the Invention

The present invention relates to a novel sulfonium salt compound, a method for producing the same, and a photoacid generator containing the sulfonium salt.

2. Background Art

Conventionally, sulfonium salt compounds have been used for various applications, such as for a photoacid generator to be used for chemically amplified resist materials. Such a chemically amplified resist material contains a resin, a photoacid generator, and a solvent. The chemically amplified resist material after being applied is irradiated with radiation such as an electron beam and X-ray within a desired region of the above-applied chemically amplified resist pattern. Thus, in response to the irradiated radiation, the photoacid generator generates an acid and the generated acid changes the solubility of the resin, which allows a resist pattern for creating an integrated circuit to be formed.

Further, integrated circuits are microfabricated in recent years. Therefore, there has been a demand for a photoacid generator having a high resolution and capable of forming a pattern with sharp edges (excellent pattern profile) in order to form a fine-scale resist pattern. As one of factors that affect the resolution and pattern profile, the acid diffusion length of the photoacid generator can be mentioned. When this acid diffusion length is large, the resolution and the precision in the pattern profile are reduced, which is commonly known.

Therefore, there is proposed a technique for suppressing the acid diffusion, for example, by employing an anion with a comparatively large volume as the anion of the photoacid generator or by introducing a polar group into the anion (see JSR TECHNICAL REVIEW No. 118, p. 8-13 (2011)). However, these methods affect the acidity or properties of the anion, and therefore there may be cases of failing to achieve the desired acidity or properties of the anion.

Then, there is proposed a photoacid generator configured to contain two kinds of sulfonium salt compounds, one of which has a comparatively strong acid anion (for example, fluorine-substituted sulfonylimide), and the other of which has a comparatively weak acid anion (for example, sulfonic acid or carboxylic acid having no fluorine substitution) (see JP 2008-7410 A). In such photoacid generator, a strong acid generated from the sulfonium salt compound having a comparatively strong acid anion by irradiation with radiation collides with the sulfonium salt compound having a comparatively weak acid anion, which has not been reacted, and this collision causes a salt exchange. As a result, the weak acid is released, whereas the released strong acid is incorporated into the sulfonium salt compound as a part thereof. Thus, the strong acid generated by irradiation with radiation is exchanged with the weak acid having a lower catalytic performance, which causes apparent inactivation of the acid, resulting in suppression of the acid diffusion.

Further, there is proposed a sulfonium salt compound having 10-camphor sulfonate anion as the sulfonium salt compound having a comparatively weak acid anion (JP 2010-215608 A). Such 10-camphor sulfonate anion is less likely to diffuse because of its high bulk structure. Accordingly, this sulfonium salt compound can suppress the acid diffusion. However, such a sulfonium salt compound generally does not have a sufficient solubility in propylene glycol 1-monomethyl ether 2-acetate (PGMEA) that is widely used for chemically amplified resist materials.

Meanwhile, i-line radiation at a wavelength of 365 nm is widely used for formation of resist patterns with large thickness using a photoacid generator. One of the reasons for that is availability of light sources such as a high-pressure mercury lamp and a metal halide lamp that allow good emission intensity of i-line light despite its low cost. Recent widespread adoption of LED lamps with an emission wavelength in the i-line region (360 to 390 nm) also can be mentioned as another reason. Molecular extinction coefficient ($\epsilon$) at 365 nm (i-line) is one of indicators for responsiveness to the i-line light.

From these reasons, photoacid generators are required to exhibit a sufficiently high responsiveness to the i-line light, as well.

However, the responsiveness is not necessarily improved simply by increasing the molecular extinction coefficient ($\epsilon$) at the i-line. For example, a sulfonium salt compound into which thioxanthone skeleton is introduced is proposed (JP 8 (1996)-165290 A); however, the sulfonium salt compound absorbs light mostly on the side of the surface on which the resist material is applied because of its excessively high molecular extinction coefficient ($\epsilon$) at 365 nm (i-line), as a result of which the light does not penetrate into a deep portion, and thus the acid generation efficiency rather tends to decrease.

Therefore, a sulfonium salt compound having a naphthalene ring in a cationic group is proposed as being useful, for example, as a photoacid generator for chemically amplified resists (see JP 2004-334060 A, JP 2006-276755 A, and JP 2010-256168 A).

SUMMARY OF THE INVENTION

However, although the molar extinction coefficient at 365 nm is improved by introducing a naphthalene ring into the sulfonium salt compound, there is no guarantee of a significant improvement in sensitivity, because of the possibility of inactivation due to fluorescence emission, even if the sulfonium salt compound could absorb light. Hence, there is also a demand for further improvement in sensitivity to radiation, in order to improve the productivity of resist patterns. Further, a sulfonium salt compound that is decomposed by brief photoirradiation and efficiently generates an acid is also desired.

It is an object of the present invention to provide a novel sulfonium salt compound capable of: generating an acid more efficiently than conventional compounds; being dissolved well in a solvent to be used for resist materials or the like; and suppressing acid diffusion when used in combination with a sulfonium salt compound that generates a stronger acid than itself, and to provide a method for producing the novel sulfonium salt compound and a photoacid generator.

As a result of diligent studies in view of the aforementioned object, the inventors of this application have found that a sulfonium salt compound represented by the following chemical formula (I), which has a cation part with a sulfonium cation structure containing a naphthyl group and an anion part with a sulfonate anion or carboxylate anion structure can generate an acid more efficiently than conventional sulfonium salt compounds, can be dissolved well in a solvent to be used for resist materials, etc., and can suppress acid diffusion when used in combination with a sulfonium salt compound that generates a stronger acid than itself. Thus, the present invention has been accomplished.

That is, the sulfonium salt compound according to the present invention is represented by the following general formula (I):

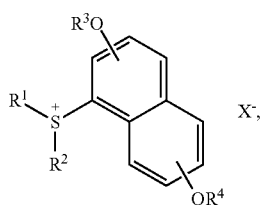
(I)

where $R^1$ and $R^2$ each denote the same or a different alkyl group having 1 to 18 carbon atoms, $R^3$ and $R^4$ each denote the same or a different alkyl group having 1 to 10 carbon atoms, $X^-$ denotes a sulfonate anion or a carboxylate anion, and the substituents denoted by $R^3O$ and $R^4O$ are each located at an arbitrary position selected from the 2-position to the 8-position of the naphthyl group.

In the sulfonium salt compound according to the present invention, it is preferable that $R^1$ and $R^2$ each be the same or a different alkyl group having 1 to 8 carbon atoms, and $R^3$ and $R^4$ each be the same or a different alkyl group having 1 to 8 carbon atoms.

In the sulfonium salt compound according to the present invention, it is preferable that $X^-$ be represented by the following general formula (II) or (III):

$R^5$—$SO_3^-$ (II), where $R^5$ denotes an adamantyl group or a 2-oxobornyl group, and

(III)

where $R^6$ denotes an adamantyl group or a 2-oxobornyl group.

In the sulfonium salt compound according to the present invention, it is preferable that $X^-$ be represented by the foregoing general formula (II), and $R^5$ be an adamantyl group or a 2-oxobornyl group.

In the sulfonium salt compound according to the present invention, it is preferable that $R^5$ be 2-oxobornyl.

The photoacid generator according to the present invention contains the aforementioned sulfonium salt compound.

The method for producing a sulfonium salt compound according to the present invention includes: a step (a) of subjecting, to dehydration condensation, a sulfoxide compound represented by the following general formula (IV):

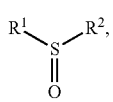
(IV)

where $R^1$ and $R^2$ each denote the same or a different alkyl group having 1 to 18 carbon atoms, and a naphthalene compound represented by the following formula (V):

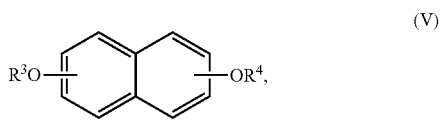
(V)

where $R^3$ and $R^4$ each denote the same or a different alkyl group having 1 to 10 carbon atoms, and the substituents denoted by $R^3O$ and $R^4O$ are each located at an arbitrary position selected from the 2-position to the 8-position of the naphthyl group; and a step (b) of producing a sulfonium salt compound represented by the following general formula (I):

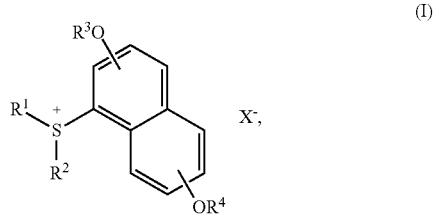
(I)

where $R^1$ and $R^2$ each denote the same constituent defined in the foregoing general formula (IV), $R^3$ and $R^4$ each denote the same constituent defined in the foregoing general formula (V), and $X^-$ is represented by the following general formula (II) or (III)

$R^5$—$SO_3^-$ (II), where $R^5$ denotes an adamantyl group or a 2-oxobornyl group, and

(III)

where $R^6$ denotes an adamantyl group or a 2-oxobornyl group, by a reaction between a dehydrated condensate obtained by the dehydration condensation in the step (a) and a salt compound or acid compound represented by a general formula $X^-Y^+$, where $X^-$ denotes the same constituent defined in the foregoing general formula (I), and $Y^+$ denotes an alkali metal ion or a hydrogen ion.

DETAILED DESCRIPTION OF THE PREFERRED EMBODIMENT

Hereinafter, embodiments of the sulfonium salt compound according to the present invention are described.

The sulfonium salt compound of the present invention is represented by the following structural formula (I):

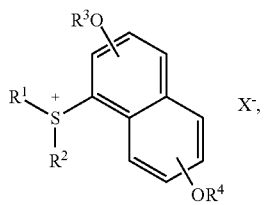

where $R^1$ and $R^2$ each denote the same or a different alkyl group having 1 to 18 carbon atoms, $R^3$ and $R^4$ each denote the same or a different alkyl group having 1 to 10 carbon atoms, $X^-$ denotes a sulfonate anion or a carboxylate anion, and the substituents denoted by $R^3O$ and $R^4O$ are each located at an arbitrary position selected from the 2-position to the 8-position of the naphthyl group.

The alkyl group having 1 to 18 carbon atoms may be straight-chained or branched-chained. Examples of the alkyl group include a methyl group, an ethyl group, a propyl group, an isopropyl group, a butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, and an octadecyl group. Among these, a butyl group is particularly preferable.

The substituents denoted by $R^1$ and $R^2$ are each preferably the same or a different alkyl group having 1 to 8 carbon atoms, more preferably the same or a different butyl group, particularly preferably a butyl group.

The substituents denoted by $R^3$ and $R^4$ are each preferably the same or a different alkyl group having 1 to 8 carbon atoms, more preferably the same or a different butyl group, particularly preferably a butyl group.

The substituents denoted by $R^3$ and $R^4$ are preferably located respectively at the 2-position and the 7-position among arbitrary positions of the 2-position to the 8-position of the naphthyl group.

As mentioned above, the cation is particularly preferably dibutyl(2,7-dibutoxynaphthalene-1-yl)sulfonium cation.

$X^-$ denotes a sulfonate anion or a carboxylate anion. $X^-$ is preferably a sulfonate anion represented by the following general formula (II), or a carboxylate anion represented by the following general formula (III):
$R^5$—$SO_3^-$ (II), where $R^5$ denotes an adamantyl group or a 2-oxobornyl group, and

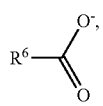

where $R^6$ denotes an adamantyl group or a 2-oxobornyl group.

Examples of the anion, represented by $X^-$, having substituents as mentioned above include (+)-2-oxo-10-bornanesulfonate anion, (±)-2-oxo-10-bornanesulfonate anion, (−)-2-oxo-10-bornanesulfonate anion, (+)-2-oxo-10-bornanecarboxylate anion, (−)-2-oxo-10-bornanecarboxylate anion, (±)-2-oxo-10-bornanecarboxylate anion, 1-adamantanecarboxylate anion, 2-adamantanecarboxylate anion, and 1-adamantanesulfonate anion.

Further, in the foregoing general formula (II), $R^5$ is preferably a 2-oxobornyl group.

According to the IUPAC nomenclature, 2-oxobornane is named as 1,7,7-trimethylbicyclo[2.2.1]heptane-2-on. Therefore, structures equivalent to 2-oxobornane may be hereinafter named in accordance with the IUPAC nomenclature in some cases.

Accordingly, the anion represented by $X^-$ is more preferably (±)-7,7-dimethyl-2-oxobicyclo[2.2.1]heptane-1-yl methanesulfonate anion, particularly preferably (1S,4R)-7,7-dimethyl-2-oxobicyclo[2.2.1]heptane-1-yl methanesulfonate anion.

Further, in the sulfonyl salt compound represented by the foregoing general formula (I), it is preferable that: $R^1$ and $R^2$ each be the same or a different alkyl group having 1 to 8 carbon atoms; $R^3$ and $R^4$ each be the same or a different alkyl group having 1 to 8 carbon atoms; the substituents denoted by $R^3$ and $R^4$ be located respectively at the 2-position and the 7-position of the naphthyl group; $X^-$ be the sulfonate anion represented by the foregoing general formula (II); and W be an adamantyl group or a 2-oxobornyl group.

Further, in the sulfonium salt compound represented by the foregoing general formula (I), it is more preferable that: $R^1$ and $R^2$ each be the same or a different alkyl group having 1 to 8 carbon atoms; $R^3$ and $R^4$ each be the same or a different alkyl group having 1 to 8 carbon atoms; the substituents denoted by $R^3$ and $R^4$ be located respectively at the 2-position and the 7-position of the naphthyl group; $X^-$ be the sulfonate anion represented by the foregoing general formula (II); and $R^5$ be a 2-oxobornyl group.

Further, the sulfonium salt compound represented by the foregoing general formula (I) is more preferably 1-(2,7-di-n-butoxynaphthyl)di-n-butylsulfonium (±)-7,7-dimethyl-2-oxobicyclo[2.2.1]heptane-1-yl methanesulfonate, particularly preferably 1-(2,7-di-n-butoxynaphthyl)di-n-butylsulfonium (1S,4R)-7,7-dimethyl-2-oxobicyclo[2.2.1]heptane-1-yl methanesulfonate.

Subsequently, a method for producing the sulfonium salt compound represented by the foregoing general formula (I) according to this embodiment is described. This sulfonium salt compound is produced, for example, using a sulfoxide compound, a naphthalene compound, and a compound represented by $X^-Y^+$, which are mentioned below, as raw materials.

Specifically, the sulfoxide compound to be used for producing the sulfonium salt compound represented by the foregoing chemical formula (I), for example, is represented by the following formula (IV):

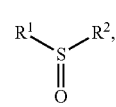

where $R^1$ and $R^2$ each denote the same or a different alkyl group having 1 to 18 carbon atoms, as mentioned above.

Specific examples of the sulfoxide compound represented by the foregoing chemical formula (IV) include diethylsulfoxide, dipropylsulfoxide, dibutylsulfoxide, dipentylsulfoxide, dihexylsulfoxide, diheptylsulfoxide, dioctylsulfoxide, dinonylsulfoxide, didodecylsulfoxide, isopropylmethylsulfoxide, methylpropylsulfoxide, butylethylsulfoxide, and methyloctylsulfoxide. Among these, the sulfoxide compound is preferably dibutylsulfoxide.

As the aforementioned sulfoxide compound, a commercially available sulfoxide compound may be used as it is, or an appropriately produced sulfoxide compound may be used. The method for producing such a sulfoxide compound is not specifically limited; for example, the sulfoxide compound can be produced with reference to a publicly known method such as methods disclosed in Tetrahedron, 57, 2469 (2001) and Molecules 12, 304 (2007).

The naphthalene compound to be used for producing the sulfonium salt compound represented by the foregoing chemical formula (I), for example, is represented by the following general formula (V):

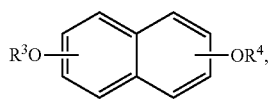

where $R^3$ and $R^4$ each denote the same or a different alkyl group having 1 to 10 carbon atoms, and the substituents denoted by $R^3O$ and $R^4O$ are each located at an arbitrary position selected from the 2-position to the 8-position of the naphthyl group.

As the naphthalene compound represented by the foregoing general formula (V), a commercially available naphthalene compound may be used as it is, or an appropriately produced naphthalene compound may be used. The method for producing such a naphthalene compound is not specifically limited; for example, the naphthalene compound can be produced with reference to a publicly known method such as methods disclosed in J. Comb. Chem., 6, 497 (2004) and Journal of Organic Chemistry, 70, 1115-1121 (2005).

Examples of the naphthalene compound include 1,5-diethoxynaphthalene, 1,5-dipropoxynaphthalene, 1,5-diisopropoxynaphthalene, 1,5-dibutoxynaphthalene, 1-ethoxy-5-methoxynaphthalene, 1-methoxy-5-propoxynaphthalene, 1-isopropoxy-5-methoxynaphthalene, 1-butoxy-5-methoxynaphthalene, 1,6-diethoxynaphthalene, 1,6-dipropoxynaphthalene, 1,6-diisopropoxynaphthalene, 1,6-dibutoxynaphthalene, 6-ethoxy-1-methoxynaphthalene, 1-methoxy-6-propoxynaphthalene, 6-isopropoxy-1-methoxynaphthalene, 6-butoxy-1-methoxynaphthalene, 1,7-diethoxynaphthalene, 1,7-dipropoxynaphthalene, 1,7-diisopropoxynaphthalene, 1,7-dibutoxynaphthalene, 7-ethoxy-1-methoxynaphthalene, 1-methoxy-7-propoxynaphthalene, 7-isopropoxy-1-methoxynaphthalene, 7-butoxy-1-methoxynaphthalene, 2, 7-diethoxynaphthalene, 2,7-dipropoxynaphthalene, 2,7-diisopropoxynaphthalene, 2, 7-dibutoxynaphthalene, 2-ethoxy-7-methoxynaphthalene, 2-methoxy-7-propoxynaphthalene, 2-isopropoxy-7-methoxynaphthalene, and 2-butoxy-7-methoxynaphthalene. Among these, 2,7-dibutoxynaphthalene is preferable.

The salt compound or acid compound to be used for producing the sulfonium salt compound represented by the foregoing general formula (I) is represented by a general formula $X^-Y^+$, where $X^-$ is represented by the following general formula (II) or (III):

$R^5$—$SO_3^-$ (II), where $R^5$ denotes an adamantyl group or a 2-oxobornyl group, and

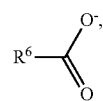

where $R^6$ denotes an adamantyl group or a 2-oxobornyl group,
and $Y^+$ denotes an alkali metal ion or a hydrogen ion.

Further, in the case where $Y^+$ is an alkali metal ion, $Y^+$ is preferably a lithium cation, a sodium cation, or a potassium cation, in view of the reactivity.

Accordingly, the salt compound represented by the foregoing general formula $X^-Y^+$ is preferably an alkali metal salt such as a sodium salt, potassium salt, or lithium salt of the anion represented by $X^-$.

Examples of the salt compound represented by the foregoing general formula $X^-Y^+$ include lithium(+)-2-oxo-10-bornanesulfonate, sodium(+)-2-oxo-10-bornanesulfonate, potassium(+)-2-oxo-10-bornanesulfonate, lithium(±)-2-oxo-10-bornanesulfonate, sodium(±)-2-oxo-10-bornanesulfonate, potassium(±)-2-oxo-10-bornanesulfonate, lithium(−)-2-oxo-10-bornanesulfonate, sodium(−)-2-oxo-10-bornanesulfonate, potassium(−)-2-oxo-10-bornanesulfonate, lithium(+)-2-oxo-10-bornanecarboxylate, sodium(+)-2-oxo-10-bornanecarboxylate, potassium(+)-2-oxo-10-bornanecarboxylate, lithium(−)-2-oxo-10-bornanecarboxylate, sodium(−)-2-oxo-10-bornanecarboxylate, potassium(−)-2-oxo-10-bornanecarboxylate, lithium(±)-2-oxo-10-bornanecarboxylate, sodium(±)-2-oxo-10-bornanecarboxylate, potassium(±)-2-oxo-10-bornanecarboxylate, lithium 1-adamantanecarboxylate, sodium 1-adamantanecarboxylate, potassium 1-adamantanecarboxylate, lithium 2-adamantanecarboxylate, sodium 2-adamantanecarboxylate, potassium 2-adamantanecarboxylate, lithium 1-adamantanesulfonate, sodium 1-adamantanesulfonate, and potassium 1-adamantanesulfonate.

Among these, the salt compound represented by the foregoing general formula $X^-Y^+$ is preferably lithium(+)-2-oxo-10-bornanesulfonate, sodium(+)-2-oxo-10-bornanesulfonate, or potassium(+)-2-oxo-10-bornanesulfonate.

Further, the acid compound represented by the foregoing general formula $X^-Y^+$ is preferably the following compounds using the anion represented by $X^-$. That is, examples of such a preferable acid compound include (+)-2-oxo-10-bornanesulfonic acid, (±)-2-oxo-10-bornanesulfonic acid, (−)-2-oxo-10-bornanesulfonic acid, (+)-2-oxo-10-bornanecarboxylic acid, (−)-2-oxo-10-bornanecarboxylic acid, (±)-2-oxo-10-bornanecarboxylic acid, 1-adamantanecarboxylic acid, 2-adamantanecarboxylic acid, and 1-adamantanesulfonic acid.

As the compound represented by the foregoing general formula $X^-Y^+$, a commercially available compound may be used as it is, or an appropriately produced compound may be used. The method for producing the $X^-Y^+$ compound is not specifically limited; for example, the $X^-Y^+$ compound can be produced with reference to a publicly known method such as methods disclosed in J. Am. Chem. Soc., 122 (30), 7390 (2000), J. Org. Chem., 67 (24), 8339 (2002), and Letters in Organic Chemistry, 4 (2), 123 (2007).

Further, in the case where the alkali metal salt is not commercially available, the alkali metal salt can be produced, for example, by neutralizing an aqueous solution of a commercially available acid represented by $X^-H^+$ with sodium hydroxide, potassium hydroxide, lithium hydroxide, or the like. In this neutralization, a hydrogen ion is converted into the aforementioned alkali metal ion. Further, the thus obtained aqueous solution of the alkali metal salt can be used as it is in the later-mentioned step (b).

The method for producing a sulfonium salt compound according to this embodiment includes: a step (a) of subjecting the sulfoxide compound represented by the foregoing general formula (IV) and the naphthalene compound represented by the foregoing general formula (V) to dehydration condensation; and a step (b) of producing the sulfonium salt compound represented by the foregoing general formula (I) by reaction between a dehydrated condensate obtained above in the step of dehydration condensation and the salt compound or acid compound represented by the foregoing general formula $X^-Y^+$.

The dehydration condensation in the step (a) and the reaction in the step (b) between the dehydrated condensate obtained in the step (a) and the salt compound or acid compound can be carried out, for example, with reference to a publicly known method such as methods disclosed in J. Org. Chem. 55, 4222 (1990), J. Chem. Soc. Chem. Commun., 470 (1991), Chem. Pharm. Bull., 29, 3753 (1981), and J. Chem. Soc. Chem. Commun., 41 (1980). Specifically, the step (a) can be performed by subjecting the sulfoxide compound and the naphthalene compound mentioned above to dehydration condensation, using a dehydrating agent as exemplified below and a strong acid such as methanesulfonic acid, in the absence of solvent or in the presence of solvent exemplified below. Further, the step (b) can be performed by subsequently allowing the condensation reaction product obtained in the step (a) to react with the compound represented by $X^-Y^+$ in the presence of solvent exemplified below.

From the viewpoint of improving the yield rate and the economic viewpoint, the above-mentioned sulfoxide compound can be used, per mole of the naphthalene compound to be used, generally at a ratio of about 0.8 to 2 mole, preferably at a ratio of about 0.9 to 1.5 mole, more preferably at a ratio of about 1.0 to 1.2 mole.

In the step (a), the dehydration condensation reaction can be carried out in the presence of a dehydrating agent. Examples of the dehydrating agent include: inorganic compounds such as diphosphorus pentoxide, sodium sulfate, and magnesium sulfate; and organic compounds such as acetic anhydride, trifluoroacetic acid anhydride, propionic acid anhydride, phthalic acid anhydride, and methanesulfonic acid anhydride. The dehydrating agent is more preferably diphosphorus pentoxide. These dehydrating agents may be used individually, or two or more of them may be used in combination.

Such a dehydrating agent can be used, per mole of the above-mentioned naphthalene compound to be used, generally at a ratio of about 0.3 to 5 mole, preferably at a ratio of about 0.4 to 3 mole, which is however not restrictive.

In the step (a), the dehydration condensation reaction can be carried out in the presence of a strong acid. Examples of the strong acid include methanesulfonic acid, ethanesulfonic acid, and sulfuric acid. The strong acid is more preferably methanesulfonic acid. These strong acids may be used individually, or two or more of them may be used in combination.

Further, the strong acid may be used in combination with the above-mentioned dehydrating agent.

Such a strong acid can be used, per mole of the naphthalene compound to be used, generally at a ratio of about 1 to 25 mole, preferably at a ratio of about 2 to 15 mole, which is however not restrictive.

A solvent may be used or may not be used in the above-mentioned step of subjecting the sulfoxide compound and the naphthalene compound to the dehydration condensation reaction in the presence of the dehydrating agent, or the like. In the case of using a solvent in this reaction, the solvent needs only to be inactive to the reactants. Specific examples of such a solvent include: chloroform; dichloromethane; ether solvents such as 1,4-dioxane, ethylene glycol dimethyl ether, diethylene glycol dimethyl ether, triethylene glycol dimethyl ether, and tetraethylene glycol dimethyl ether; nitrile solvents such as acetonitrile, propionitrile, and butyronitrile; amides such as N,N-dimethylformamide, N,N-dimethylacetamide; and sulfolane. These solvents can be used individually, or two or more of them can be mixed for use. The reaction solvent can be used, per 100 parts by weight of the naphthalene compound, generally in an amount of about 30 to 3000 parts by weight, preferably in an amount of about 50 to 2000 parts by weight.

As a procedure in the dehydration condensation reaction, there can be mentioned a method, for example, in which the naphthalene compound, the dehydrating agent, etc., and the reaction solvent, etc., are mixed and stirred in specific amounts, and the sulfoxide compound is added thereto in a specific amount, which is however not restrictive.

The dehydration condensation reaction is carried out at a reaction temperature of generally $-20°$ C. to $100°$ C., preferably $-10°$ C. to $80°$ C., more preferably $0°$ C. to $40°$ C.

In the step (b), the procedure in the above-mentioned reaction between the product of the dehydration condensation reaction and the compound represented by $X^-Y^+$ (that is, salt exchange reaction) is not specifically limited. Examples of such a procedure include: (1) a procedure in which an aqueous solution is prepared by adding a specific amount of the compound represented by $X^-Y^+$ to a specific amount of water, and thereafter this aqueous solution is added to the reaction solution after the above-mentioned dehydration condensation reaction, (2) a procedure in which an aqueous solution is prepared by adding a specific amount of the compound represented by $X^-Y^+$ to a specific amount of water, and thereafter the reaction solution after the above-mentioned dehydration condensation reaction is added to this aqueous solution, (3) a procedure in which a specific amount of the compound represented by $X^-Y^+$ is added to the reaction solution after the above-mentioned dehydration condensation reaction, (4) a procedure in which the reaction solution after the above-mentioned dehydration condensation reaction is added to a specific amount of the compound represented by $X^-Y^+$, (5) a procedure in which an aqueous solution of the product of the dehydration condensation reaction is formed by adding the reaction solution after the above-mentioned dehydration condensation reaction to a specific amount of water, and thereafter a specific amount of the compound represented by $X^-Y^+$ is added to this aqueous solution, and (6) a procedure in which an aqueous solution of the product of the dehydration condensation reaction is formed by adding the reaction solution after the above-mentioned dehydration condensation reaction to a specific amount of water, and thereafter this aqueous solution is added to a specific amount of the compound represented by $X^-Y^+$. In the above-mentioned reaction, organic solvents such as dichloromethane and chloroform may be further added.

The compound represented by $X^-Y^+$ can be used, per mole of the naphthalene compound used in the aforementioned step (a), generally at a ratio of about 0.8 to 2 mole, preferably about 0.9 to 1.3 mole, which is however not restrictive. Use of the compound represented by $X^-Y^+$ at a ratio of 0.8 mole or more can sufficiently suppress the decrease in yield rate.

Further, use of this compound at a ratio of 2 mole or less allows proper effects corresponding to the used amount to be sufficiently obtained, which is therefore more economical.

It should be noted that this compound represented by $X^-Y^+$ can be added in the form of an aqueous solution as mentioned above.

Further, the above-mentioned alkali metal salt compounds, for example, can be used as the compound represented by $X^-Y^+$. Further, a commercially available alkali metal salt compound can be used therefor. However, in the case where no commercially available alkali metal salt compounds can be found, the above-mentioned commercially available acid compound represented by $X^-Y^+$ (that is, an acid compound represented by $X^-H^+$) is neutralized with sodium hydroxide, potassium hydroxide, lithium hydroxide, or the like, in an aqueous solution so as to be converted into alkali metal salt, which can be used in the form of an aqueous solution of alkali metal salt, for example.

Further, there may be a case where a desired amount of the reaction product cannot be obtained when the reaction between a specific amount of the product of the dehydration condensation reaction and a specific amount of the compound represented by $X^-Y^+$ (salt exchange reaction) is caused by adding a specific amount of the compound represented by $X^-Y^+$. If this is because the compound represented by $X^-Y^+$ is insufficient and thus the salt exchange reaction has not been completed, the following procedure can be taken, for example. That is, water or an organic solvent such as dichloromethane and chloroform is added to the reaction solution after salt exchange, as needed, the reaction solution is then separated into an aqueous layer and an organic layer, and the compound represented by $X^-Y^+$ is further added to the resultant organic layer. Thereafter, the salt exchange reaction may be carried out again. In this procedure, the compound represented by $X^-Y^+$ is added in an amount, preferably in the range of 0.05 to 0.5 times the initially added amount, more preferably in the range of 0.05 to 0.2 times that amount.

In the step (b), the salt exchange reaction can be carried out at a reaction temperature of generally about −10 to 100° C., preferably about 0 to 60° C. When the reaction temperature is −10° C. or more, a sufficiently high reaction speed and a comparatively short reaction time can be achieved. Further, when the reaction temperature is 100° C. or less, it is possible to suppress side reactions, thereby suppressing the decrease in purity and yield rate.

After the completion of the reaction, the thus obtained sulfonium salt compound can be isolated, for example, by carrying out a procedure in which a precipitated solid is separated by filtration, or a procedure in which, after the reaction product is extracted using an organic solvent such as monochlorobenzene, ethyl acetate, and dichloromethane, the organic solvent is distilled off. Further, the sulfonium salt compound can be refined, as needed, by a conventional method such as column chromatography, charcoal treatment, and recrystallization using a solvent, e.g., ethyl acetate, dichloromethane, methyl-t-butyl ether, isopropyl ether, monochlorobenzene, n-heptane, n-hexane, methanol, and water.

Due to having a higher sensitivity to radiation, particularly to radiation of the i-line region, than conventional sulfonium salt compounds, the sulfonium salt compound of this embodiment is decomposed by brief photoirradiation and can generate an acid more efficiently than conventional sulfonium salt compounds. Further, this sulfonium salt compound is dissolved well in a solvent to be used for resist materials, etc. In particular, the sulfonium salt compound exhibits good solubility in PGMEA, which is a solvent generally used for chemically amplified resist materials. Moreover, the sulfonium salt compound can suppress acid diffusion when used in combination a sulfonium salt compound that generates a stronger acid than itself.

Other than radiation of the i-line region, examples of radiation include far-ultraviolet ray radiation, broad radiation (three wavelength lines of g, h, and i), KrF (248 nm) excimer laser radiation, ArF (193 nm) excimer laser radiation, $F_2$ (157 nm) excimer laser radiation, electron beam radiation, and soft X-ray radiation.

Subsequently, the photoacid generator of this embodiment is described.

The photoacid generator of this embodiment according to the present invention contains the sulfonium salt compound represented by the foregoing chemical formula (I). This photoacid generator may contain a single kind of the sulfonium salt compound alone, or may contain two or more kinds of the sulfonium salt compound and other sulfonium salt compounds in combination.

The photoacid generator can be used for chemically amplified resist materials. Such a chemically amplified resist material, for example, contains the photoacid generator, a resin, and a solvent capable of dissolving the photoacid generator and the resin.

Examples of the resin include a resin curable by polymerization with an acid. When the chemically amplified resist material containing such a resin is applied and irradiated with radiation in a desired pattern, an acid is generated in the irradiated portion, and this acid causes the irradiated portion to be cured. Then, the uncured portion is removed by a solvent capable of dissolving the resin, so that a so-called negative resist pattern is obtained. In this regard, examples of the resin include novolac epoxy resins, hydroxypolystyrene resins, and alkali-soluble phenol resins. Further, examples of radiation include far-ultraviolet ray radiation, broad radiation (three wavelength lines of g, h, and i), KrF (248 nm) excimer laser radiation, ArF (193 nm) excimer laser radiation, $F_2$ (157 nm) excimer laser radiation, electron beam radiation, and soft X-ray radiation, other than radiation of the i-line region.

In addition to above, examples of the resin include a resin into which a protecting group imparting insolubility in an alkali aqueous solution is introduced, and which can be dissolved in the alkali aqueous solution when the protecting group is eliminated by an acid. When the chemically amplified resist material containing such a resin is applied and irradiated with the above-mentioned radiation in a desired pattern, an acid is generated in the irradiated portion, and this acid causes the elimination of the protecting group in the irradiated portion. Then, the irradiated portion is removed by the alkali aqueous solution, so that a so-called positive resist pattern is obtained. In this regard, examples of the resin include polyvinylphenol resins, acrylic resins, polynorbornene resins, fluorine resins, and novolac resins as shown in the later-mentioned examples.

Further, in the case where the photoacid generator is used for a chemically amplified resist material, it is preferable that the photoacid generator contain a first onium salt compound and a second onium salt compound as two kinds of onium salt compounds, the first onium salt compound be the sulfonium salt compound represented by the foregoing general formula (I), and the second onium salt compound generate a stronger acid than the first onium salt compound in response to radiation.

Examples of the onium salts include iodonium salt, other than the sulfonium salt mentioned above.

This allows the photoacid generator, when a chemically amplified resist material containing the photoacid generator is applied onto a circuit board, or the like, and irradiated with radiation in a desired pattern, to generate an acid (first acid) from the first onium salt compound and a stronger acid (second acid) from the second onium salt compound than from the first onium salt compound. Since a stronger acid is generated from the second onium salt compound, a resist pattern is formed mainly by the second onium salt compound. At this time, when the second acid generated from the second onium salt compound collides with an unreacted anion that is a source of the first acid in the first onium salt compound, the comparatively weak first acid is released by salt exchange, instead of which an anion part that is a source of the second acid and a cation part represented by the foregoing general formula (I) form a salt together. In this way, the second acid is exchanged with the weaker first acid. That is, the second acid is exchanged with the first acid having a weaker influence (lower catalytic performance) of acid on the resin. Thus, it is made possible to control the acid diffusion.

The strength of the acid to be generated can be determined, for example, by the quantity of fluorine at the α-position or β-position of the anionic substituent having an anionic structure in the onium salt compounds. Specifically, an onium salt compound having an anion in which all the hydrogen atoms are substituted by fluorine atoms (complete substitution) or a part of a plurality of hydrogen atoms are substituted by fluorine atoms (multiple substitution), for example, can be determined to generate a comparatively stronger acid than an onium salt compound having an anion in which no hydrogen atoms are substituted by fluorine atoms.

Examples of the second onium salt compound include 1-(2,7-di-n-butoxynaphthyl)di-n-butylsulfonium di(1,1,2,2,3,3,4,4,4-nonafluorobutanesulfone)imido.

Further, the photoacid generator can be used for photocurable resin materials, other than chemically amplified resist materials mentioned above. Such a photocurable resin material, for example, contains: the photoacid generator; a monomer, oligomer, or polymer that is cured by polymerization with an acid as mentioned above; and a solvent capable of dissolving the photoacid generator and the monomer, oligomer, or polymer therein. Then, when the photocurable resin material is applied and irradiated with the radiation light, an acid is generated in the irradiated portion, and the irradiated portion is cured by this acid. In this regard, examples of the resin include epoxy resins, oxetane resins, and vinyl ether resins.

The sulfonium salt compound of this embodiment can be used for applications, for example, as a photoacid generator for chemically amplified resist materials in which an acid generated by irradiation with radiation, particularly light rays is utilized. Such a photoacid generator, for example, is used suitably for chemically amplified resist materials to be used for producing semiconductors, TFTs, color filters, micromachine parts, or the like.

Further, the sulfonium salt compound of this embodiment can be used for other applications in which an acid generated by irradiation with radiation, particularly light rays, serves as a catalyst. Such a photoacid generator can be used for applications, for example, as a catalyst for polymerization reactions or crosslinking reactions. This photoacid generator enables a curable compound to be surely polymerized within a short time and a cured product having good properties to be obtained.

As has been described above, due to having a higher sensitivity to radiation, particularly radiation of the i-line region, than conventional sulfonium salt compounds, the sulfonium salt compound of this embodiment represented by the foregoing general formula (I) is decomposed by brief photoirradiation and can generate an acid more efficiently than conventional sulfonium salt compounds. Further, this sulfonium salt compound is dissolved well in a solvent to be used for resist materials, etc. Particularly, the sulfonium salt compound exhibits good solubility in PGMEA, which is a solvent generally used for resist materials. Furthermore, the sulfonium salt compound can suppress acid diffusion when used in combination a sulfonium salt compound that generates a stronger acid than itself.

Thus, this embodiment provides a novel sulfonium salt compound that generates an acid more efficiently than conventional sulfonium salt compounds, that is dissolved well in a solvent to be used for resist materials, etc., and that can suppress acid diffusion when used in combination with a sulfonium salt compound that generates a stronger acid than itself. This embodiment also provides a method for producing the novel sulfonium salt compound and a photoacid generator.

EXAMPLES

Hereinafter, the present invention is described in detail by way of examples. However, the present invention is not limited to these examples.

Example 1

Production of 1-(2,7-di-n-butoxynaphthyl)di-n-butylsulfonium (1S,4R)-7,7-dimethyl-2-oxobicyclo[2.2.1]heptane-1-yl methanesulfonate (Procedure 1)

Diphosphorus pentoxide (3.41 g) and methanesulfonic acid (23.07 g) were put into a reaction container. Further, 2,7-dibutoxynaphthalene (16.34 g) and dibutylsulfoxide (12.66 g) were added thereto, and the mixture was stirred at room temperature for 16 hours. While the temperature within the reaction container was maintained at 0 to 10° C., deionized water (100 g) was added thereto, and a 20%-NaOH aqueous solution (80 g) was further added dropwise thereto. After the dropwise addition, dichloromethane (80 g) was added thereto, allowed to stand still, and separated into layers. Thereafter, the aqueous layer was removed. The thus obtained organic layer was washed with deionized water (60 g) and thereafter they were separated into layers, from which the aqueous layer was removed. Thus, a reaction solution of a condensation reaction product was obtained.

(Procedure 2)

Deionized water (70 g), (1S,4R)-7,7-dimethyl-2-oxobicyclo[2.2.1]heptane-1-yl methanesulfonate (13.94 g), and sodium hydroxide (2.4 g) were put into another reaction container. The entire amount of the reaction solution of the condensation reaction product was added thereto, and the mixture was stirred at room temperature for 20 minutes. The reaction solution was allowed to stand still so as to be separated into layers, from which the aqueous layer was removed. Thus, an organic layer was obtained.

(Procedure 3)

Deionized water (70 g), (1S,4R)-7,7-dimethyl-2-oxobicyclo[2.2.1]heptane-1-yl methanesulfonate (0.70 g), and sodium hydroxide (0.12 g) were put into yet another reaction container. The entire amount of the organic layer obtained above by Procedure 2 was added thereto, and the mixture was stirred at room temperature for 20 minutes. The resultant reaction solution was allowed to stand still so as to be separated into layers, from which the aqueous layer was removed. Thus, an organic layer was obtained.

(Procedure 4)

The organic layer obtained above by Procedure 3 was filtrated and washed with deionized water. Thereafter, the organic layer was fractionated. From this organic layer, dichloromethane was distilled off. To the thus obtained concentrate was added t-butylmethyl ether (MTBE) (156 g) at 50° C., and the mixture was crystallized. Thus, 35.05 g of white crystal of 1-(2,7-di-n-butoxynaphthyl)di-n-butyl sulfonium (1S,4R)-7,7-dimethyl-2-oxobicyclo[2.2.1]heptane-1-yl methanesulfonate (Example compound 1) was obtained.

As shown below, the results of analysis of the white crystal obtained above by Procedures 1 to 4 using $^1$H-NMR and LC-MS demonstrated that the white crystal contained $R^1$, $R^2$, $R^3$, and $R^4$ each being a butyl group and $X^-$ being (1S,4R)-7,7-dimethyl-2-oxobicyclo[2.2.1]heptane-1-yl methanesulfonate, in the general formula (I).

$^1$H-NMR (400 MHz; DMSO-$d_6$; Internal Standard Substance: Tetramethylsilane): δ (ppm) 0.75 (s, 3H), 0.82 (t, J=7.3 Hz, 6H), 0.97 (t, J=7.3 Hz, 3H), 1.00 (t, J=7.3 Hz, 3H), 1.07 (s, 3H), 1.22-1.66 (m, 14H), 1.74-1.98 (m, 7H), 2.24 (m, 1H), 2.38 (d, J=14.6 Hz, 1H), 2.73 (m, 1H), 2.89 (d, J=14.6 Hz, 1H), 3.84-4.04 (m, 4H), 4.18 (t, J=6.5 Hz, 2H), 4.45 (t, J=6.5 Hz, 2H), 7.24 (dd, J=2.2 and 9.0 Hz, 1H), 7.52 (d, J=2.2 Hz, 1H), 7.59 (d, J=9.3 Hz, 1H), 8.02 (d, J=9.0 Hz, 1H), 8.38 (d, J=9.3 Hz, 1H)

MS (LC/ESI(+)Spectrum): $M^+$ 417
MS (LC/ESI(−)Spectrum): $M^-$ 231

Comparative Example 1

Production of triphenylsulfonium (1S,4R)-7,7-dimethyl-2-oxobicyclo[2.2.1]heptane-1-yl methanesulfonate (Procedure 1)

Deionized water (10 g), (1S,4R)-7,7-dimethyl-2-oxobicyclo[2.2.1]heptane-1-yl methanesulfonate (1.39 g), and sodium hydroxide (0.24 g) were put into a reaction container. Further, dichloromethane (20 g) and triphenylsulfonium bromide (2.06 g) were added thereto, and the mixture was stirred at room temperature for 20 minutes. The resultant reaction solution was allowed to stand still so as to be separated into layers, from which the aqueous layer was removed. Thus, an organic layer was obtained.

(Procedure 2)

Deionized water (10 g), (1S,4R)-7,7-dimethyl-2-oxobicyclo[2.2.1]heptane-1-yl methanesulfonate (0.14 g), and sodium hydroxide (0.03 g) were put into another reaction container. Further, the entire amount of the organic layer obtained above by Procedure 1 was added thereto, and the mixture was stirred at room temperature for 20 minutes. The reaction solution was allowed to stand still so as to be separated into layers, from which the aqueous layer was removed. Thus, an organic layer was obtained.

(Procedure 3)

Deionized water (10 g), (1S,4R)-7,7-dimethyl-2-oxobicyclo[2.2.1]heptane-1-yl methanesulfonate (0.07 g), and sodium hydroxide (0.02 g) were put into yet another reaction container. Further, the entire amount of the organic layer obtained above by Procedure 2 was added thereto, and the mixture was stirred at room temperature for 20 minutes. The resultant reaction solution was allowed to stand still so as to be separated into layers, from which the aqueous layer was removed. Thus, an organic layer was obtained.

(Procedure 4)

The organic layer obtained above by Procedure 3 was filtrated and washed with deionized water. Thereafter, the organic layer was fractionated. From this organic layer, dichloromethane was distilled off. Thus, 2.82 g of white crystal of triphenylsulfonium (1S,4R)-7,7-dimethyl-2-oxobicyclo[2.2.1]heptane-1-yl methanesulfonate (Comparative Example compound 1) was obtained.

As shown below, the results of analysis of the white crystal obtained above by Procedure 1 to Procedure 4 using $^1$H-NMR and LC-MS demonstrated that the white crystal was triphenylsulfonium (1S,4R)-7,7-dimethyl-2-oxobicyclo[2.2.1]heptane-1-yl methanesulfonate.

$^1$H-NMR (400 MHz; CDCl$_3$; Internal Standard Substance: Tetramethylsilane): δ (ppm) 0.83 (s, 3H), 1.16 (s, 3H), 1.30 (m, 1H), 1.67 (m, 1H), 1.82 (m, 1H), 1.90-2.05 (m, 2H), 2.29 (m, 1H), 2.76-2.96 (m, 2H), 3.38 (m, 1H), 7.63-7.76 (m, 9H), 7.80-7.92 (m, 6H)

MS (LC/ESI(+)Spectrum) $M^+$ 263
MS (LC/ESI(−)Spectrum): $M^-$ 231

Reference Example 1

Production of 1-(2,7-di-n-butoxynaphthyl)di-n-butylsulfonium di(1,1,2,2,3,3,4,4,4-nonafluorobutanesulfone)imido (Procedure 1)

Diphosphorus pentoxide (1.7 g) and methanesulfonic acid (11.5 g) were put into a reaction container. Further, 2,7-dibutoxynaphthalene (8.2 g) and dibutylsulfoxide (6.3 g) were added thereto, and the mixture was stirred at room temperature for 16 hours. While the temperature within the reaction container was maintained at 0 to 10° C., a 20%-NaOH aqueous solution (30 g) was added dropwise thereto, and dichloromethane (80 g) was further added thereto. The mixture was allowed to stand still so as to be separated into layers, from which the aqueous layer was removed. Thus, an organic layer was obtained. The thus obtained organic layer was washed with deionized water (30 g) and thereafter they were allowed to stand still so as to be separated into layers, from which the aqueous layer was removed. Thus, a reaction solution of a condensation reaction product was obtained.

(Procedure 2)

Deionized water (30 g) and potassium bis(nonafluorobutanesulfone)imido (18.6 g) were put into another reaction container. Further, the entire amount of the reaction solution obtained above by Procedure 1 was added thereto, and the mixture was stirred at room temperature for 20 minutes. Thereafter, insoluble matter was filtrated. The thus obtained filtrate was allowed to stand still so as to be separated into layers, from which the aqueous layer was removed. Thus, an organic layer was obtained.

(Procedure 3)

From the organic layer obtained above by Procedure 2, dichloromethane was distilled off. To the thus obtained concentrate were added MTBE (17 g) and hexane (34 g) at 50° C., and the mixture was crystallized. Thus, 18.8 g of white crystal of 1-(2,7-di-n-butoxynaphthyl)di-n-butylsulfonium di(1,1,2,2,3,3,4,4,4-nonafluorobutanesulfone)imido (Reference Example compound 1) was obtained.

The results of analysis of the thus obtained white crystal using $^1$H-NMR and LC-MS demonstrated below that the white crystal contained $R^1$, $R^2$, $R^3$, $R^4$ each being a butyl group and $X^-$ being di(1,1,2,2,3,3,4,4,4-nonafluorobutanesulfone)imido anion, in the general formula (I).

¹H-NMR (400 MHz; DMSO-$d_6$; Internal Standard Substance: Tetramethylsilane): δ (ppm) 0.82 (t, J=7.3 Hz, 6H), 0.97 (t, J=7.3 Hz, 3H), 1.00 (t, J=7.3 Hz, 3H), 1.30-1.65 (m, 12H), 1.74-1.96 (m, 4H), 3.81-4.04 (m, 4H), 4.18 (t, J=6.6 Hz, 2H), 4.44 (t, J=6.6 Hz, 2H), 7.24 (dd, J=2.2 and 9.0 Hz, 1H), 7.50 (d, J=2.2 Hz, 1H), 7.57 (d, J=9.0 Hz, 1H), 8.01 (d, J=9.0 Hz, 1H), 8.36 (d, J=9.0 Hz, 1H)

MS (LC/ESI(+)Spectrum): M⁺ 417
MS (LC/ESI(−)Spectrum): M⁻ 580

(Solubility)

To the sulfonium salt compound to be measured (test compound; 100 mg each) was added PGMEA, and a strong shaking for 30 seconds was repeated at 20±5° C. every 5 minutes. In this way, the amount of PGMEA necessary for dissolving the test compound after 30 minutes was measured. Here, "dissolving" means to reach the state where no insoluble matter can be observed by visual inspection, specifically, means that the resultant solution is clear, or a mixture in an arbitrary ratio becomes transparent.

As the measurement results, Table 1 below shows the amount (mL) of PGMEA necessary for dissolving each test compound. In Table 1 below, the compounds that require PGMEA in an amount of 16 mL or less were evaluated as having desirable properties as a current target compound.

TABLE 1

| Test Compound | PGMEA (mL) |
|---|---|
| Example Compound 1 | 11 |
| Comparative Example Compound 1 | >160 |

(Measurement of Ultraviolet-Visible Absorption Spectrum)

A 1×10⁻⁴ mol/L acetonitrile solution of each test compound was prepared, and the molecular extinction coefficient at 365 nm in the ultraviolet-visible absorption spectrum was measured using an ultraviolet-visible spectrophotometer (UV-2400PC, manufactured by SHIMADZU CORPORATION). Table 2 shows the results. Considering that light should be transmitted to a deep portion in a thick film, compounds with a molecular extinction coefficient at 365 nm (i-line) of 50 to 2000 were evaluated as a compound having desirable properties.

TABLE 2

| Test Compound | Molecular Extinction Coefficient (365 nm) |
|---|---|
| Example Compound 1 | 640 |
| Comparative Example Compound 1 | 0 |

Example 2 and Comparative Example 2

Preparation of Positive Resist Composition
(Chemically Amplified Resist Material)

Each sulfoxide compound was mixed at a mixing ratio shown in Table 3 to prepare the photoacid generator of Example 2 and Comparative Example 2. Further, the thus obtained photoacid generator and each resin were uniformly dissolved in PGMEA at a mixing ratio shown in Table 3, and the thus obtained solution was filtrated through a membrane filter with a pore size of 1 μm. Thus, each positive resist composition was prepared.

In Table 3, Resin A and Resin B each indicate the following material, and the figures each indicate a mixed amount (parts by mass).

Resin A: Novolac resin (resin, having a molecular weight of 8000, obtained by addition condensation of m/p-cresol=6/4 and formaldehyde in the presence of an acid catalyst)

Resin B: Compound represented by the following general formula (VI):

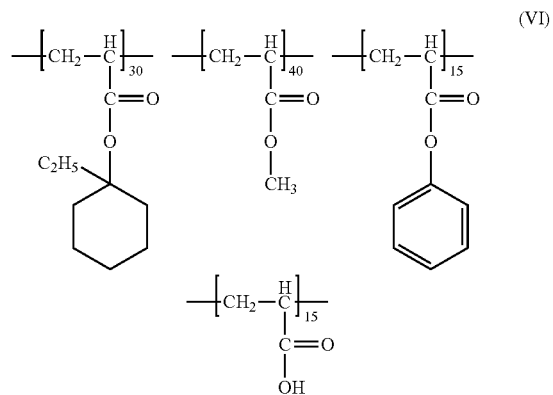

TABLE 3

| | Positive Resist Composition | | | | |
|---|---|---|---|---|---|
| | Photoacid Generator | | | | |
| | Reference Example compound 1 | Example compound 1 | Resin A | Resin B | PGMEA |
| Example 2 | 2.0 | 0.2 | 50 | 50 | 115 |
| Comparative Example 2 | 2.0 | — | 50 | 50 | 115 |

(Formation of Resist Pattern)

A positive photoresist composition containing the photoacid generator of each of Example 2 and Comparative Example 2 obtained as mentioned above was applied onto an 8-inch copper substrate using a spinner, and the applied photoresist composition was dried. Thus, a photoresist layer having a film thickness of 20 μm was obtained. Subsequently, this resist layer was placed on a hot plate and pre-baked at 140° C. for 5 minutes.

The pre-baked photoresist layer was exposed using an exposure apparatus, NSR-i14E (manufactured by Nikon; NA: 0.54; σ: 0.59). Subsequently, the exposed photoresist layer was placed on the hot plate, and subjected to post-exposure bake (PEB) at 85° C. for 3 minutes. Thereafter, a 2.38% tetramethylammonium hydroxide (TMAH) aqueous solution was added dropwise to the photoresist layer, which was then left standing for 60 seconds at 23° C. The procedure from the dropwise addition of the TMAH aqueous solution to leaving of the photoresist layer at 23° C. for 60 seconds was repeated 4 times. Then, development was performed. Thereafter, it was washed in running water and blow-dried with nitrogen. Thus, a resist in a 10-μm line and space pattern was obtained. The cross sectional profile of this line and space pattern was observed using a scanning electron microscope (Product name: SU-8000, manufactured by Hitachi High-Technologies Corporation). Those having a rectangular cross sectional profile were evaluated as ○ (excellent), and those having a tapered cross sectional profile that becomes thinner toward the tip were evaluated as x (poor). Table 4 shows the results.

TABLE 4

| | Pattern Profile |
|---|---|
| Example 2 | ○ |
| Comparative Example 2 | x |

The resist composition containing the photoacid generator of Comparative Example 2 failed to have a preferable pattern profile because of its poor control of acid diffusion, whereas the resist composition containing the photoacid generator of Example 2 had an excellent pattern profile. That is, a photoacid generator that enables formation of an excellent pattern profile was obtained by adding Example compound 1 to Reference Example compound 1. It should be noted that Reference Example compound 1 having a fluorine-substituted anionic structure generates a stronger acid than Example compound 1 having no fluorine substitution. In this way, considering that Reference Example compound 1 generates a stronger acid than Example compound 1, Example compound 1 can be recognized as a compound that exhibits excellent control of acid diffusion when combined with a sulfonium salt compound that generates a stronger acid than itself.

The above results show that the sulfonium salt compound of the present invention and a photoacid generator containing this compound are capable of generating an acid more efficiently than conventional sulfonium salt compounds, being dissolved well in a solvent to be used for resist materials, etc., and suppressing acid diffusion when used in combination with a sulfonium salt compound that generates a stronger acid than itself. Further, in addition to ease of adjustment of resist sensitivity, it is possible to suppress the rate of acid diffusion within the resist film so as to improve the resolution and suppress the change in sensitivity after exposure. Moreover, it is possible to reduce the dependency on the substrate or the environment so as to further improve the exposure latitude, the pattern profile, or the like.

Industrial Applicability

The present invention can be used as a photoacid generator for chemically amplified resist materials, and can be used as a photoacid generator in combination with a sulfonium compound that generates a comparatively strong acid. In addition, the present invention is expected to be used, for example, as a polymerization initiator used in combination with a curable resin that is cured by polymerization with an acid.

What is claimed is:

1. A sulfonium salt compound represented by the following general formula (I):

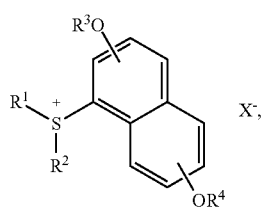

(I)

where $R^1$ and $R^2$ each denote a butyl group, $R^3$ and $R^4$ each denote the same or a different alkyl group having 1 to 10 carbon atoms, $X^-$ denotes a sulfonate anion represented by the following general formula (II):
$R^5$—$SO_3^-$ (II), where denotes a 2-oxobornyl group, and the substituents denoted by $R^3O$ and $R^4O$ are each located at an arbitrary position selected from the 2-position to the 8-position of the naphthyl group.

2. The sulfonium salt compound according to claim 1, wherein
$R^3$ and $R^4$ are each the same or a different alkyl group having 1 to 8 carbon atoms.

3. A photoacid generator containing the sulfonium salt compound according to claim 1.

4. A method for producing a sulfonium salt compound, comprising:
a step (a) of subjecting, to dehydration condensation, a sulfoxide compound represented by the following general formula (IV):

(IV)

where $R^1$ and $R^2$ each denote a butyl group,
and a naphthalene compound represented by the following formula (V):

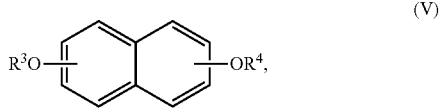

(V)

where $R^3$ and $R^4$ each denote the same or a different alkyl group having 1 to 10 carbon atoms, and the substituents denoted by $R^3O$ and $R^4O$ are each located at an arbitrary position selected from the 2-position to the 8-position of the naphthyl group; and
a step (b) of producing a sulfonium salt compound represented by the following general formula (I):

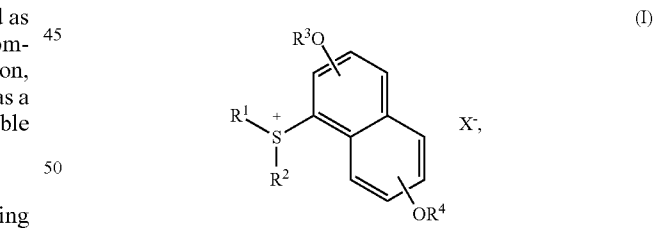

(I)

where $R^1$ and $R^2$ each denote the same constituent defined in the foregoing general formula (IV), $R^3$ and $R^4$ each denote the same constituent defined in the foregoing general formula (V), and $X^-$ is represented by the following general formula (II):
$R^5$—$SO_3^-$ (II), where $R^5$ denotes a 2-oxobornyl group,
by a reaction between a dehydrated condensate obtained by the dehydration condensation in the step (a) and a salt compound or acid compound represented by a general formula $X^-Y^+$, where $X^-$ denotes the same constituent defined in the foregoing general formula (II), and $Y^+$ denotes an alkali metal ion or a hydrogen ion.

* * * * *

UNITED STATES PATENT AND TRADEMARK OFFICE
CERTIFICATE OF CORRECTION

PATENT NO. : 8,952,204 B2  Page 1 of 1
APPLICATION NO. : 14/095870
DATED : February 10, 2015
INVENTOR(S) : Hironori Kinoshita It is certified that error appears in the above-identified patent and that said Letters Patent is hereby corrected as shown below:

Specification

In column 4 at line 40 (approx.), Change "(III)" to --(III):--.

In column 6 at line 24 (approx.), Change "W" to --$R^5$--.

Claims

In column 20 at line 3, In Claim 1, change "where" to --where $R^5$--.

Signed and Sealed this
Tenth Day of November, 2015

Michelle K. Lee
*Director of the United States Patent and Trademark Office*